(12) United States Patent
Powell

(10) Patent No.: US 8,790,721 B2
(45) Date of Patent: Jul. 29, 2014

(54) COMPOSITIONS AND METHODS FOR TREATING THE SYMPTOMS ASSOCIATED FOR ALCOHOL BASED HANGOVERS

(71) Applicant: The Esmond Company, LLC, Dover, DE (US)

(72) Inventor: Melissa Largey Powell, Tampa, FL (US)

(73) Assignee: The Esmond Company, LLC

( * ) Notice: Subject to any disclaimer, the term of this patent is extended or adjusted under 35 U.S.C. 154(b) by 0 days.

(21) Appl. No.: 13/898,422

(22) Filed: May 20, 2013

(65) Prior Publication Data
US 2013/0309331 A1    Nov. 21, 2013

Related U.S. Application Data

(60) Provisional application No. 61/649,327, filed on May 20, 2012.

(51) Int. Cl.
*A01N 65/00* (2009.01)

(52) U.S. Cl.
USPC .............................................. 424/725

(58) Field of Classification Search
None
See application file for complete search history.

(56) References Cited

U.S. PATENT DOCUMENTS

2007/0217967 A1*  9/2007  McDermott et al. .......... 422/168

* cited by examiner

*Primary Examiner* — Michael Meller
(74) *Attorney, Agent, or Firm* — Innovus Law Group, PLLC; Thomas E. Toner

(57) ABSTRACT

Compositions and methods that are effective relieving the symptoms of an alcoholic induced hangover, comprising of an acidified, protonated and mechanical excited pre-mix blended with a sweet, pleasant tasting mixture of vitamins, minerals, spices and natural herbs in an enriched aqueous composition.

1 Claim, 2 Drawing Sheets

FIG. 2

| Ingredients | 1 | 2 | 3 | 4 | 5 | 6 |
|---|---|---|---|---|---|---|
| Premix | 0.10 | 0.25 | 0.35 | 0.50 | 0.75 | 1.00 |
| B6 | .00013 | 0.00013 | 0.00013 | 0.00013 | 0.00013 | 0.00013 |
| B 12 | 0.000024 | 0.000024 | 0.000024 | 0.000024 | 0.000024 | 0.000024 |
| C | 0.012 | 0.012 | 0.012 | 0.012 | 0.012 | 0.012 |
| Magnesium | 0.41 | 0.41 | 0.41 | 0.41 | 0.41 | 0.41 |
| Potassium | 3.5 | 3.5 | 3.5 | 3.5 | 3.5 | 3.5 |
| Zinc | 0.015 | 0.015 | 0.015 | 0.015 | 0.015 | 0.015 |
| Milk Thistle | 0.2 | 0.2 | 0.2 | 0.2 | 0.2 | 0.2 |
| Ginger | 2.0 | 2.0 | 2.0 | 2.0 | 2.0 | 2.0 |
| Xylitol | 4.0 | 4.0 | 4.0 | 4.0 | 4.0 | 4.0 |
| Sugar | 4.0 | 4.0 | 4.0 | 4.0 | 4.0 | 4.0 |
| Flavor | trace | trace | trace | trace | trace | trace |
| Color | trace | trace | trace | trace | trace | trace |
| Carrier | Balance | Balance | Balance | Balance | Balance | Balance |

… # COMPOSITIONS AND METHODS FOR TREATING THE SYMPTOMS ASSOCIATED FOR ALCOHOL BASED HANGOVERS

CROSS REFERENCE TO RELATED APPLICATIONS

This application is a Non-Provisional Application of U.S. Provisional Application No. 61/649,327 filed May 20, 2012, which is incorporated herein by reference.

FIELD OF THE INVENTION

The present disclosure relates to compositions and methods that are effective relieving the symptoms of an alcoholic induced hangover

BACKGROUND OF THE INVENTION

A hangover is a group of unpleasant signs and symptoms that can develop after drinking too much alcohol. The more alcohol you drink, the more likely you are to have a hangover the next day. The alcohol passes through the stomach and into the bloodstream, which distributes it throughout the body, irritating and even damaging cells and cell membranes. Alcohol metabolism that is more toxic than alcohol itself, acetaldehyde, is created when the alcohol in the liver is broken down. This produces a double effect of toxins in the body. The acetaldehyde is automatically attacked by another enzyme and a substance called glutathione. The process works well, leaving the acetaldehyde only a short time to affect the body. This is true only if a small of alcohol is consumed. The amount of glutathione stored in the liver is quickly depleted when larger amount of alcohol is consumed. The acetaldehyde builds up in the body, causing headaches and vomiting, basically, a hangover.

The primary cause of hangovers is due to effects of by-products of the alcohol fermentation. These elements cause symptoms when they reach your bloodstream and trigger a reaction in your body. There are 22 common signs associated with a hangover but the most common ones are Headache, Dehydration, Difficulties concentrating, Shakiness, Rapid heartbeat, bloodshot eyes, Vomiting, Dizziness and Hypersensitivity to light and noises.

SUMMARY OF INVENTION

The disclosed compositions and methods that effective are relieving the symptoms of an alcoholic induced hangover.

The disclosed compositions comprise an acidified, protonated and mechanical excited pre-mx blended with a sweet, tasting mixture of vitamins and supplement in an enriched aqueous composition.

BRIEF DESCRIPTION OF THE DRAWINGS

For a fuller understanding of the invention, reference should be made to the following detailed description, taken in connection with the accompanying drawings, in which:

FIG. 2 is a table of non-limiting examples of the disclosed compositions.

DETAILED DESCRIPTION OF THE PREFERRED EMBODIMENT

Figure 1:
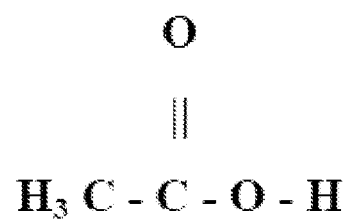
FIG. 1 shows the structure of acetic acid.

When alcohol is consumed, it enters the bloodstream and causes the pituitary gland in the brain to block the creation of vasopressin, a known as the antidiuretic hormone. Without this chemical, the kidneys then send water directly to the bladder instead of reabsorbing it into the body, causing the drinkers have to make frequent trips to the bathroom after urinating for the first time after drinking. Once absorbed by the bloodstream, the alcohol leaves the body in three ways:

1) The kidney eliminates 5 percent of alcohol in the urine.
2) The lungs exhale 5 percent of alcohol, which can be detected by a breathalyzer.
3) The liver chemically breaks down the remaining alcohol into acetic acid.

The breakdown, or oxidation, of ethanol occurs in the liver where the enzyme in the liver called alcohol dehydrogenase strips electrons from ethanol to form acetaldehyde. Another enzyme, called aldehyde dehydrogenase, converts the acetaldehyde, in the presence of oxygen, to acetic acid, the main component in vinegar. The molecular structure of acetic acid is shown in FIG. 1.

When ethanol is oxidized to acetic acid, two protons and two electrons are also produced. The acetic acid can be used to form fatty acids or can be further broken down into carbon dioxide and water.

This diuretic effect decreases as the alcohol in the bloodstream decreases, but the aftereffects help create a hangover. The morning after heavy drinking, the body sends a desperate message to replenish its water supply usually manifested in the form of an extremely dry mouth. Headaches result from dehydration because the body's organs try to make up for their own water loss by stealing water from the brain, causing the brain to decrease in size and pull on the membranes that connect the brain to the skull, resulting in pain. The frequent urination also expels salts and potassium that are necessary for proper nerve and muscle function; when sodium and potassium levels get too low, headaches, fatigue and nausea can result.

Alcohol also breaks down the body's store of glycogen in the liver, turning the chemical into glucose and sending it out of the body in the urine. In addition, the diuretic effect expels vital electrolytes such as potassium and magnesium, which are necessary for proper cell function. Although body weight is a factor, part of the reason women should not keep up with men drink-for-drink is because women have less acetaldehyde dehydrogenase and glutathione, making their hangovers worse because it takes longer for the body to break down the alcohol.

Because alcohol is absorbed directly through the stomach, the cells that line the organ become irritated. Alcohol also promotes secretion of hydrochloric acid in the stomach, eventually causing the nerves to send a message to the brain that the stomach's contents are hurting the body and must be expelled through vomiting.

The human body can remove alcohol already absorbed in your bloodstream in a few different ways. These are metabolism, evaporation through your breath and excretion through urinating, sweating, tears and the sorts. There are also many people who can actually begin breaking down the alcohol while in their stomachs, before it is absorbed into the bloodstream through higher levels of the enzymes called alcohol dehydrogenase which convert the alcohol into a toxic acetaldehyde. Then the next set of enzymes called acetaldehyde dehydrogenase break it all down into the non-toxic acetic acid.

Hypoglycemia, Dehydration, Acetaldehyde, Intoxication, and Vitamin B12 deficiency are all theorized causes of hangover symptoms. The cause of a hangover can be best explained by the following:

1) The increased Nicotinamide Adenine Dinucleotide, abbreviated NAD+ production during metabolism of alcohol by the enzymes.
2) This enzyme is called alcohol dehydrogenase and aldehyde dehydrogenase, excess NADH can build up and slow down sugar breakdown in the liver, thus causing Hypoglycemia.

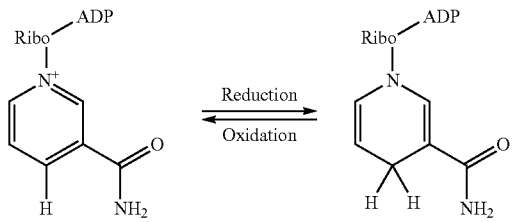

3) 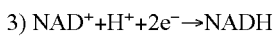 NAD+ + H+ + 2e− → NADH
4) Hypoglycemia is the medical term for a pathologic state produced by a lower than normal level of sugar in the blood.
5) This produces a variety of symptoms and effects but the principal problems arise from an inadequate supply of glucose (sugar) as fuel to the brain, resulting in impairment of function.
6) Alcohol has a dehydrating effect by causing increased urine production. Dehydration causes the brain to shrink away from the skull slightly. This can be mitigated by drinking water or an oral electrolytes solution after consumption of alcohol.
7) Alcohol's effect on the stomach lining can account for nausea.

Treatment

Currently, there are no drugs which can be taken in order to speed up one's metabolism of alcohol; however, carbonated beverages will speed up metabolism in general.

Herbal compounds have become increasingly popular for hangovers. These include ingredients such as milk thistle, guava leaf and ginseng, which aim to boost bio-chemicals that help the body to deal with toxins. The evidence to support these ingredients are difficult to find.

Supplements such as magnesium during a hangover can help replace the magnesium depleted from your body while it processed the alcohol.

Studies have shown B6 as effective towards helping the body cope with the stress on the body that occurs when it exposed to alcohol, preservatives and some congeners which cause heightened hangovers.

Adding salt and sugar to water helps to replace the sodium and glycogen lost the night before. Fruit juice is has a positive effect since the sugar helps to increase the body's energy, while the vitamins and nutrients can help to replace the depleted minerals due to alcohol's diuretic effect. Also, bouillon soup helps your hangover as it replaces salt and potassium lost while the alcohol was being consumed.

In recent years there have been several new products which are herbal, vitamin or chemical blends that claims to cure hangovers. Products like Chasers, Xo3, First Call, Hangover Defense are just a few examples that is on the market today.

The above criteria should be used as discriminating factors that are effective relieving the symptoms of an alcoholic induced hangover.

Hangover treatments must be effective to reduce several of the effects especially headaches, fatigue, thirst, poor sleep, dizziness, decreased ability to concentrate, bloodshot eyes, sensitivity to light and sound shakiness, nausea, vomiting and stomach pains. To be effective the composition must achieve five factors: (1) it must be able to metabolize the alcohol to be effective, (2) it must be exposed to the alcohol long enough to be effective, (3) the product must remain active in the environment in which it is used, (4) it must not be inhibit the production of the enzyme, alcohol dehydrogenase, and (5) it must be able to counteract the effects of hypoglycemia to be effective.

Application methods for the treatment in the hangover relief include liquid and pill form.

Pre-Mix Blend

The present invention starts with the mixture of hydrogen sulfate with urea in a ratio of 1.5:1 and 6.5:1. This mixture is added to water in a 1:1 ratio to 4:1. This is exothermic and should be done is a glass container. The mixture is rapidly cooled to room temperature to allow the addition of carborane most particularly, trifluoromethanesulfonic acid (also known as triflic acid, or TfOH). The carborane is added previous mixture at a ratio of 1:1.75 to 1:7. This creates a mineral salt of organic amide. Immediately two steel rods of 3/16 alloy 20 steel material is inserted into the container and using a DC charger a predetermined amperage/voltage is pulsed through the mixture for 1 hour. The pulse sequence ranges from 20 to 70 seconds intervals. This acidic composition after being "excited" displays a maximum proton count of $1.5 \times 10^{25}$, and conductivity range of from 800 mV to 1200 mV. This mixture is will be used in the Hangover Cure and is referred to as "The PRE-MIX". The premix is then mixed with vitamins B6, B12, C and Magnesium, Potassium and Zinc; and natural herbs such as milk thistle; sweeteners consisting of monosaccharides, disaccharides or polysaccharides and polyols such as glucose, dextrose, maltodextrins, fructose, maltose, sucrose, honey, corn syrup solids, lactose, xylitol, erythritol, aspartame, stevia, sucralose, mannitol, sorbitol, maltitol, lactitol, ribitol, saccharin and xylose.

However, other non-limiting embodiments and combinations are possible as further disclosed herein.

Carriers

The balance of the disclosed compositions comprises a carrier. The carrier can be any suitable material that can dissolve the active ingredients and co-ingredients and deliver the biocidal system to the affected person being treated. Water is a convenient carrier for liquid embodiments of the disclosed composition. Flavors are optional and can be incorporated in the carrier.

Formulations

FIG. 2 provides a table of non-limiting examples of the disclosed compositions.

Methods of Use

The disclosed compositions can be used as an oral dose that is ingested before bedtime after alcohol has been consumed. The dosage is effective in relieving the symptoms of an alcoholic induced hangover and usage regimen is dictated by the needs and demand of the individual. Liquid applications usually consist of a composition that is enough to make mixed with the already consumed alcohol. The composition converts the alcohol to a carboxylic acid and also acts as a catalyst to convert the NADH to NAD+ which reduces the effects of hangover. Pill applications are effective where the dosage is taken in the same manner as the liquid dosage.

Examples

The term "effective amount" as used herein means "an amount of a composition as disclosed herein, effective at dosages and for periods of time necessary to achieve the desired result." An effective amount may vary according to factors known in the art, such as the state, age, species, and size of the area being treated. Although particular dosage regimes may be described in examples herein, a person skilled in the art would appreciated that the dosage regime may be altered to provide optimum therapeutic response.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense. Any materials, which may be cited above, are fully incorporated herein by reference.

It is also to be understood that the following claims are intended to cover all of the generic and specific features of the invention herein described, and all statements of the scope of the invention which, as a matter of language, might be said to fall therebetween. Relative terminology, such as "substantially" or "about," describe the specified materials, steps, parameters or ranges as well as those that do not materially affect the basic and novel characteristics of the claimed inventions as whole (as would be appreciated by one of ordinary skill in the art). Now that the invention has been described,

What is claimed is:

1. A composition for treating a hangover in a human in need thereof consisting essentially of therapeutically effective amounts of urea, hydrogen sulfate and trifluoromethanesulfonic acid.

* * * * *